United States Patent [19]

Sato et al.

[11] Patent Number: 5,608,089
[45] Date of Patent: Mar. 4, 1997

[54] PROCESS FOR PRODUCING CIS-EPOXYSUCCINATES

[75] Inventors: Keiichi Sato, Tokyo; Kenji Murayama, Machida; Kazutaka Ida, Yokohama, all of Japan

[73] Assignee: Mitsubishi Chemical Corporation, Tokyo, Japan

[21] Appl. No.: 481,393

[22] PCT Filed: Jan. 17, 1994

[86] PCT No.: PCT/JP94/00053

§ 371 Date: Aug. 24, 1995

§ 102(e) Date: Aug. 24, 1995

[87] PCT Pub. No.: WO94/17049

PCT Pub. Date: Aug. 4, 1994

[30] Foreign Application Priority Data

Jan. 19, 1993 [JP] Japan .................................. 5-068349
May 18, 1993 [JP] Japan .................................. 5-116212

[51] Int. Cl.⁶ ..................... C07D 301/12; C07D 303/48
[52] U.S. Cl. ............................................................ 549/531
[58] Field of Search ............................................... 549/531

[56] References Cited

U.S. PATENT DOCUMENTS 3,156,709 11/1964 Allan ....................................... 549/531
3,769,339 10/1973 Wagner et al. ......................... 549/531
4,026,908 5/1977 Pralus et al. ........................... 549/531
4,065,475 12/1977 Hosoi et al. ............................ 549/531

FOREIGN PATENT DOCUMENTS 100119 2/1984 European Pat. Off. .............. 549/531
2347224 4/1974 Germany .
51-20490 12/1976 Japan .
137913 12/1978 Japan .................................... 549/531
54-29486 12/1979 Japan .

Primary Examiner—Joseph E. Evans
Attorney, Agent, or Firm—Oblon, Spivak, McClelland, Maier & Neustadt, P.C.

[57] ABSTRACT

A process for producing a highly pure cis-epoxysuccinate in a high yield while suppressing a production of DL-tartrate as a by-product by epoxidizing a maleate with hydrogen peroxide in the presence of an epoxidation catalyst, wherein said epoxidation is carried out in an aqueous solution containing 30 to 90% by volume of a water-soluble alcohol. It is possible to recycle the mother liquor separated of the formed cis-epoxysuccinate to the reaction system. The obtained cis-epoxysuccinate is useful as a polymer resin additive, a detergent builder(surfactant) and an intermediate for producing tartaric acid.

6 Claims, No Drawings

PROCESS FOR PRODUCING CIS-EPOXYSUCCINATES

TECHNICAL FIELD

The present invention relates to a process for producing cis-epoxysuccinates. More specifically, the present invention relates to a process for producing highly pure cis-epoxysuccinates in a highly yield while suppressing the production of DL-tartrate produced as a by-product, by epoxidizing maleates with hydrogen peroxide in the presence of an epoxidation catalyst.

BACKGROUND OF THE INVENTION

In the past, there has been known a process for producing cis-epoxysuccinates, which comprises reacting maleates with hydrogen peroxide in an aqueous solution in the presence of an epoxidation catalyst such as tungstate or molybdate (G. B. Payne, J. Org. Chem. 24, 54, 1959). That process, however, when industrially applied, has suffered from the disadvantages of failing to avoid a large admixture of catalyst in the produced cis-epoxysuccinates, leading to not only the loss of the product quality but also the insufficiency of the recycling of an expensive catalyst, and as a result, it has seemed difficult of industrial practice also from the economical point of view.

There has also been proposed an improved process therefor, which is intended for producing an acid salts of cis-epoxysuccinic acid having a smaller water solubility than that of a normal salts of cis-epoxysuccinic acid, so that the catalyst may be more easily separated therefrom (Japanese Patent Publication (KOKOKU) No. 51-20490 and Japanese Patent Publication (KOKOKU) No. 54-29486). However, according to these prior processes, since pH of the reaction solution is in the acid range, the produced acid salts of cis-epoxysuccinic acid are further hydrolyzed to be converted to DL-tartrate. The production of DL-tartrate not only may bring about the loss of the product quality as well as that of the yield per unit weight of the starting maleate and hydrogen peroxide, but also the produced DL-tartrate may act as an epoxidation inhibitor. Consequently, it becomes necessary that such DL-tartrate is eliminated by any means, thereby disadvantageously complicating the catalyst recycling step. There can be considered an improved process therefor, wherein pH of the reaction solution is maintained in the neutral range. In such case, however, the yield of the acid salts of cis-epoxysuccinic acid may be remarkably decreased.

DISCLOSURE OF THE INVENTION

An object of the present invention is to provide an industrially advantageous production process of cis-epoxysuccinates, which improves the disadvantages of the previous processes for producing cis-epoxysuccinates.

Specifically, a process for producing a cis-epoxysuccinate comprising epoxidizing a maleate with hydrogen peroxide in the presence of an epoxidation catalyst, wherein the epoxidation is conducted in an aqueous solution containing 30 to 90% by volume of a water-soluble alcohol, whereby a highly pure cis-epoxysuccinic acid salt can be obtained in a high yield, while suppressing the production of DL-tartrate produced as a by-product. Further, it is possible to recycle a mother liquor freed of the produced cis-epoxysuccinate, by adding to a mother liquor a calcium compound and an alkali so that the tartrate produced as a by-product can precipitate in the form of calcium tartrate which is then separated and removed out of the system.

THE BEST MODE FOR ENFORCING THE INVENTION

The present invention will be described in more detail in the following.

According to the present invention, there can be produced acid salts of cis-epoxysuccinic acid which may easily be converted to cis-epoxysuccinic acid and normal salts of cis-epoxysuccinic acid. One of the conditions to be specified for producing acid salts of cis-epoxysuccinic acid is that maleates are acid salts of maleic acid. For instance, when acid salts of maleic acid produced by reacting maleic anhydride or maleic acid with equimolar amount of a base thereto is present in a reaction system, thus produced acid salts of maleic acid can easily be epoxidized with hydrogen peroxide in the presence of an epoxidation catalyst to obtain acid salts of cis-epoxysuccinic acid. Specifically, maleic anhydride or maleic acid is previously reacted with equimolar amount of a base thereto, thereby producing acid salts of maleic acid, which then is subjected to the epoxidation reaction. Alternatively, maleic anhydride or maleic acid may be introduced into the epoxidation reaction system simultaneously with equimolar amount of a base thereto without preliminary salt-forming reaction. In such case, since the acid salts of maleic acid are readily produced and thereafter the epoxidation reaction proceeds, only the acid salts of cis-epoxysuccinic acid is substantially produced. Likewise, maleic anhydride or maleic acid may be introduced into the epoxidation reaction system simultaneously with equimolar amount of a maleic normal salt. Also in such case, since the acid salts of maleic acid are readily produced and thereafter the epoxidation reaction proceeds, only the acid salts of cis-epoxysuccinate acid are substantially produced.

Furthermore, when a base is used in a molar amount a little more or a little less than that of maleic anhydride or maleic acid, the epoxidation of the normal salts of maleic acid or free maleic acid is carried out to produce the corresponding cis-epoxysuccinic acid or normal salts thereof. In such case, so far as a compound having maleic skeleton is epoxidized and the produced compound is mainly acid salts of a cis-epoxysuccinic acid, such a compound is of course included in the scope of the present invention.

According to the present invention, it is essential for the reaction to be conducted under the conditions which can produce acid salts of cis-epoxysuccinic acid. In case when the main product is cis-epoxysuccinic acid, the pH of the reaction solution is shifted more to the acid side, thereby increasing the amount of DL-tartrate produced as a by-product. On the other hand, when the main product is normal salts of cis-epoxysuccinic acid which has a higher solubility than that of acid salts thereof, it becomes impossible to obtain the objective product in a high yield. In addition, under the conditions in which the normal salts of cis-epoxysuccinic acid is produced, normal salts of maleic acid having a very poor solubility in the presence of a water-soluble alcohol is also produced. Hence, it occurs the problem that the normal salts of maleic acid is admixed in large quantities in the obtained normal salts of cis-epoxysuccinic acid.

Acid salts of cis-epoxysuccinic acid produced according to the present invention are acid salts of monoacidic bases such as sodium hydrogen cis-epoxysuccinate, potassium hydrogen cis-epoxysuccinate and ammonium hydrogen cis-epoxysuccinate. Thus, as the maleates which are used as starting materials in the present invention, sodium hydrogen maleate, potassium hydrogen maleate and ammonium hydrogen maleate may be exemplified.

As the bases which is used for producing acid salts of maleic acid, bases which react with maleic acid or maleic anhydride, such as sodium hydroxide, potassium hydroxide and ammonium hydroxide may be exemplified. As the normal salts of maleic acid which also is used for producing maleic acid salts, disodium maleate, dipotassium maleate and diammonium maleate may be exemplified.

According to the present invention, the amount of hydrogen peroxide used is 0.5 to 2 mol, preferably 1 to 1.5 mol based on 1 mol of maleate. Hydrogen peroxide is usually added in the form of an aqueous solution. When used in such form, an aqueous solution containing 30 to 60% by weight of hydrogen peroxide is used in usual, but an aqueous solution containing 30 to 50% by weight of hydrogen peroxide is preferable in viewpoint of safety.

Epoxidation catalysts which is used in the present invention include tungstic acid or salts thereof, molybdic acid or salts thereof, and heteropolyacids containing tungsten or molybdenum, or salts thereof, which are preferably water-soluble. Specifically, sodium tungstate, sodium molybdate, phosphorus tungstate, phosphorus molybdate, silicotungstate and the like may be exemplified. Among them, sodium tungstate is more preferred. The amount of the used catalyst relative to maleate is an amount which would be conventionally used in the epoxidation reaction, but it is usually the range of $1 \times 10^{-3}$ to $5 \times 10^{-1}$, preferably $5 \times 10^{-3}$ to $1 \times 10^{-1}$ (in molar ratio).

According to the present invention, it is required that the reaction is conducted in an aqueous solution containing 30 to 90% by volume of a water-soluble alcohol. The "water-soluble alcohol" herein means an alcohol which can dissolve at amounts of not less than 10 g in 100 g of water at room temperature. Specifically, methanol, ethanol, n-propanol, iso-propanol, iso-butanol, sec-butanol, tert-butanol, tertpentyl alcohol, ethylene glycol, propylene glycol, 1,3-propanediol, 1,4-butanediol, glycerin and the like may be exemplified. Among them, ($C_1$–$C_4$) water-soluble alcohol is preferred, and in particular, methanol, ethanol and ethylene glycol are more preferred. It is considered that the addition of a water-soluble alcohol to water not only lowers the solubility of the produced acid salts of cis-epoxysuccinic acid, thereby producing a large amount of crystal of acid salts of cis-epoxysuccinic acid, but also lowers the concentration of acid salts of cis-epoxysuccinic acid in the reaction solution, which also display an effect of suppressing the production of DL-tartrate as a by-product.

The amount of water-soluble alcohol to be used is in the range of 30 to 90% by volume, preferably 50 to 90% by volume based on the total volume of aqueous solution. When the amount of the water-soluble alcohol is less than 30% by volume, the solubility of the produced acid salts of cis-epoxysuccinic acid cannot be sufficiently lowered, hence the objective product obtained in the form of crystal may be lowered and the amount of DL-tartrate as a by-product may be increased. When the amount of the water-soluble alcohol is more than 90% by volume, the solubility of the acid salts of maleic acid which substantially serves as reaction substrate may be largely lowered, hence an industrially practicable reaction rate cannot be attained.

In order to obtain a highly pure acid salts of cis-epoxysuccinic acid in a high yield in the present invention, it is preferred that the reaction is carried out at pH of 2.5 to 4.5. If the pH values is more than 4.5, the epoxidation reaction may be accelerated, but the yield of the acid salts of cis-epoxysuccinic acid may largely lower and the decomposition of hydrogen peroxide may be accelerated, thus such pH value is not preferred. If the pH values is less than 2.5, the amount of produced DL-tartrate as a by-product may be increased as a result of the hydrolysis of the produced acid salts of cis-epoxysuccinic acid, hence such pH value also is not preferred.

The reaction of the process according to the present invention is carried out at a temperature of 30° to 70° C., preferably 40° to 60° C., for 0.5 to 10 hours, preferably 0.5 to 5 hours.

It is preferable that the mother liquor freed of the produced cis-epoxysuccinate is recycled for reuse, since such mother liquor contains unreacted maleate, unrecovered cis-epoxysuccinate and epoxidation catalyst. In the case of such recycling, however, a tartrate produced as a by-product through the reaction should be removed from the mother liquor to the outside of the system, since such tartrate may inhibit the epoxidation reaction. Though the reaction inhibiting mechanism by the tartrate has not yet been elucidated, it is believed that the tartrate reacts with an epoxidation catalyst to form a complex compound, thereby causing the lowering of the catalytic performance of the epoxidation catalyst.

In order to separate the tartrate from the mother liquor, the tartrate may be precipitated in the form of calcium tartrate tetrahydrate. For that purpose, to the mother liquor, a calcium compound such as calcium hydroxide is added at not less than equimolar amount relative to the tartrate in the mother liquor, then an alkali such as sodium hydroxide is added at not less than equimolar amount relative to the total of unreacted maleate and unrecovered cis-epoxysuccinate in the mother liquor so that the solubility of the unreacted maleate and the unrecovered cis-epoxysuccinate may be increased, and thus the tartrate may be separated by precipitation in the form of calcium tartrate. In such case, as calcium compounds, calcium carbonate and the like may be cited in addition to calcium hydroxide as mentioned above. Also, as alkalis, sodium hydroxide, potassium hydroxide, ammonium hydroxide and the like may be exemplified. It is preferred to use the same alkali as that used in the epoxidation reaction system.

According to the above described procedure, it is possible that the tartrate produced as a by-product in the mother liquor is separated therefrom by precipitation and then the resulting mother liquor is recycled. Namely, to the mother liquor which has been freed of the cis-epoxysuccinate, are added a calcium compound at not less than equimolar amount, preferably 1 to 2 molar amount relative to the tartrate, and an alkali at not less than equimolar amount, preferably 1 to 2 molar amount relative to the total of unreacted maleate and unrecovered cis-epoxysuccinate so that the tartrate may be precipitated in the form of calcium tartrate, and then the resultant mother liquor may be subjected to heat-treatment as desired for causing to decompose the unreacted hydrogen peroxide. The heat-treatment is carried out at a temperature in the range of 30 to 70° C., preferably 40° to 60° C. for 0.5 to 10 hours, preferably 0.5 to 3 hours. Then, the reaction solution is subjected to the concentration treatment by evaporation for balancing the total water content thereof in such a way that both of water introduced into the system along with the starting aqueous hydrogen peroxide and water used for the washing of crystal is removed out of the system. At the same time, water-soluble alcohol can be recovered for recycling. Thereafter, the precipitated calcium tartrate is separated from the mother liquor by subjecting to filtration and the like. To the thus treated mother liquor, are added a prescribed amount of maleate and a water-soluble alcohol. Then, a prescribed amount of hydrogen peroxide to carry out the epoxidation reaction. It is preferred that maleic acid or maleic anhydride is added to the mother liquor in an amount corresponding to the total of calcium compound and alkali used for the separation of tartrate. In this way, the recycling system of an industrially favorable process for producing cis-epoxysuccinates was established.

The present invention will be more concretely explained by way of the following examples, but the invention is not restricted only to the examples unless it does not exceed beyond the scope of the gist of the invention.

EXAMPLE 1

Into a 100 ml 4-necked flask equipped with a cooler, 19.21 g (0.1 mol) of sodium hydrogen maleate trihydrate, 0.33 g (1.0 mmol) of sodium tungstate dihydrate as catalyst and 40 ml of an aqueous solution containing 50% by volume of ethanol were introduced, then heated to 50° C. 11.2 ml (0.11 mol) of a 30% aqueous hydrogen peroxide solution was added thereto, then the reaction was initiated. 7N sodium hydroxide was added for adjusting the pH value to 3.5 during the reaction. After allowed to react for 3 hours, the reaction solution was cooled to 4° C., the precipitated sodium hydrogen cis-epoxysuccinate was filtered off in the form of crystal. The reaction solution after cooled had a pH of 4.7. The crystal filtered off was washed with 40 ml of an aqueous solution containing 50% by volume of ethanol, then dried. In this way, 12.3 g of sodium hydrogen cis-epoxysuccinate was obtained as crystal. Thus obtained crystal was subjected to quantitative analysis, which were perproduced by using high performance liquid chromatography for cis-epoxysuccinate, maleate and tartrate, and by using fluorescent X ray spectroscopy for tungstate. The results showed that the crystal contained 0.09% by weight of maleate and 23 ppm of tungstate only, whereas no tartrate was detected. The filtrate and the washings were also subjected to quantitative analysis by using high performance liquid chromatography. The results summed up of both of the above quantitative analysis showed that the conversion ratio of sodium hydrogen maleate was 90.9% and the each yield of sodium hydrogen cis-epoxysuccinate and tartrate (molar yield based on the maleate) were 89.2% and 1.7%.

EXAMPLE 2

The same reaction as Example 1 was carried out except that 9.8 g (0.1 mol) of maleic anhydride and 4.17 g (0.1 mol) of 96% sodium hydroxide were used in place of sodium hydrogen maleate trihydrate, and 12.5 g of sodium hydrogen cis-epoxysuccinate was obtained as crystal. The conversion ratio of maleic anhydride was 86.0% and each yield of sodium hydrogen cis-epoxysuccinate and tartrate were 84.2% and 1.8%.

COMPARATIVE EXAMPLE 1

The same reaction as Example 2 was carried out except that 40 ml of water was used in place of an aqueous solution containing 50% by volume of ethanol, and the conversion ratio of maleic anhydride of 86.6% and each yield of sodium hydrogen cis-epoxysuccinate and tartrate of 85.0% and 1.6% were obtained, however the yield of the sodium hydrogen cis-epoxysuccinate as crystal was only 1.4 g. Thus the effect of use of a mixed solvent of water and a water-soluble alcohol of the present invention has been definitely shown.

EXAMPLE 3

The same reaction as Example 2 was carried out except that methanol was used in place of ethanol, and 11.1 g of sodium hydrogen cis-epoxysuccinate was obtained as crystal. The conversion ratio of maleic anhydride was 75.5% and each yield of sodium hydrogen cis-epoxysuccinate and tartrate were 75.5% and trace amounts.

EXAMPLE 4

The same reaction as Example 2 was carried out except that ethylene glycol was used in place of ethanol, and 9.9 g of sodium hydrogen cis-epoxysuccinate was obtained as crystal. The conversion ratio of maleic anhydride was 85.4% and each yield of sodium hydrogen cis-epoxysuccinate and tartrate were 83.7% and 1.7%.

EXAMPLE 5

The same reaction as Example 2 was carried out except that 1,4-butanediol was used in place of ethanol, and 11.3 g of sodium hydrogen cis-epoxysuccinate was obtained as crystal. The conversion ratio of maleic anhydride was 87.1% and each yield of sodium hydrogen cis-epoxysuccinate and tartrate were 85.1% and 2.0%.

EXAMPLE 6

The same reaction as Example 1 was carried out except that an aqueous solution having the alcohol content of 75% by volume was used, and 14.2 g of sodium hydrogen cis-epoxysuccinate was obtained as crystal. The conversion ratio of sodium hydrogen maleate was 91.5% and each yield of sodium hydrogen cis-epoxysuccinate and tartrate were 90.1% and 1.4%.

EXAMPLE 7

The same reaction as Example 6 was carried out except that the methanol was used in place of ethanol, and 15.2 g of sodium hydrogen cis-epoxysuccinate was obtained as crystal. The conversion ratio of sodium hydrogen maleate was 96.6% and each yield of sodium hydrogen cis-epoxysuccinate and tartrate were 94.7% and 1.9%.

EXAMPLE 8

The same reaction as Example 6 was carried out except that ethylene glycol was used in place of ethanol, and 12.4 g of sodium hydrogen cis-epoxysuccinate was obtained as crystal. The conversion ratio of sodium hydrogen maleate was 93.1% and each yield of sodium hydrogen cis-epoxysuccinate and tartrate were 90.8% and 2.3%.

EXAMPLE 9

Into an 1 liter 4-necked flask equipped with a cooler, 192.1 g (1 mol) of sodium hydrogen maleate trihydrate, 3.3 g (10 mmol) of sodium tungstate dihydrate as catalyst and 400 ml of an aqueous solution containing 75% by volume of ethanol were introduced, then heated to 60° C. 122.5 ml (1.2 mol) of a 30% aqueous hydrogen peroxide solution was added thereto over a period of 1 hour, then the reaction was initiated. After allowed to react for 4 hours, the reaction solution was cooled to 5° C., the precipitated sodium hydrogen cis-epoxysuccinate was filtered off in the form of crystal. The crystal which had been filtered off was washed with 250 ml of water, then dried. In this way, 135.2 g of sodium hydrogen cis-epoxysuccinate was obtained as crystal. The conversion ratio of sodium hydrogen maleate was 97.7% and each yield of sodium hydrogen cis-epoxysuccinate and tartrate were 93.2% and 2.1%.

The total volume of the mother liquor obtained from the above reaction was divided into 10 equal portions. To one portion thereof, sodium hydroxide was added in an amount of 0.36 g (9.06 mmol) at equimolar amount to the total of unreacted sodium hydrogen maleate and unrecovered sodium hydrogen cis-epoxysuccinate. Then calcium hydroxide was added in an amount of 0.14 g (1.90 mmol) at equimolar amount to the tartrate produced as a by-product, and the reaction solution was subjected to heat-treatment at 45° C. for 1 hour. Thereafter, the reaction solution was concentrated under reduced pressure to reach the total volume of 10 ml for the purpose of recovering methanol and at the same time balancing the water content. After allowed to cool to room temperature, the precipitated calcium tartrate was filtered off. The mother liquor freed of the calcium tartrate was recycled to the epoxidation system. Namely, the mother liquor was added with 19.2 g (0.1 mol) of sodium hydrogen maleate trihydrate and 30 ml of methanol, then heated to 60° C. 12.25 ml (0.12 mol) of a 30% hydrogen peroxide solution was added thereto over a period of 1 hour, then the reaction was initiated. After allowed to react for 3 hours, the reaction solution was cooled to 5° C., whereby 11.3 g of sodium hydrogen cis-epoxysuccinate was obtained as crystal. The conversion ratio of sodium hydrogen maleate was 85.0% and each yield of sodium hydrogen cis-epoxysuccinate and tartrate were 86.7% and 0.7%.

EXAMPLE 10

The reaction was conducted in a similar manner to that of Example 9, was carried out except that for separating the tartrate by precipitation in the form of calcium tartrate, calcium hydroxide in an amount of 0.28 g (3.80 mmol) corresponding to 2 molar amount to the tartrate produced as a by-product was added. 13.0 g of sodium hydrogen cis-epoxysuccinate was obtained as crystal. The conversion ratio of sodium hydrogen maleate was 97.3% and each yield of sodium hydrogen cis-epoxysuccinate and tartrate were 96.1% and 0.7%.

EXAMPLE 11

Into a 200 ml 4-necked flask equipped with a cooler, 38.4 g (0.2 tool) of sodium hydrogen maleate trihydrate, 0.66 g (2 mmol) of sodium tungstate dihydrate as catalyst and 80 ml of an aqueous solution containing 75% by volume of methanol were introduced, then heated to 60° C. 24.5 ml (0.24 mol) of a 30% aqueous hydrogen peroxide solution was added thereto over a period of 30 minutes, then the reaction was initiated. After allowed to react for 3 hours, the reaction solution was cooled to 5° C., the precipitated sodium hydrogen cis-epoxysuccinate was filtered off in the form of crystal. The crystal filtered off was washed with 40 ml of an aqueous solution containing 75% by volume of methanol, and then dried. In this way, 29.8 g of sodium hydrogen cis-epoxysuccinate was obtained as crystal. The conversion ratio of sodium hydrogen maleate was 99.3% and each yield of sodium hydrogen cis-epoxysuccinate and tartrate was 89.4% and 1.2%.

The mother liquor obtained from the above reaction was added with 0.26 g (6.39 mmol) of sodium hydroxide and 0.32 g (4.38 mmol) of calcium hydroxide, then subjected to heat-treatment at 45° C. for 1 hour. Then the reaction solution was concentrated under reduced pressure to reach the total volume of 20 ml for the purpose of recovering methanol and at the same time, balancing the water content. After allowed to cool to room temperature, the precipitated calcium tartrate was filtered off. The mother liquor freed of the calcium tartrate was added with 1.41 g (12.2 mmol) of maleic acid, then recycled to the epoxidation system. Namely, the mother liquor was added with 36.1 g (0.1878 mol) of sodium hydrogen maleate trihydrate and 60 ml of methanol, then heated to 60° C. After allowed to react and subjected to post-treatment in the same manner as described above, 30.6 g of sodium hydrogen cis-epoxysuccinate was obtained as crystal. The conversion ratio of sodium hydrogen maleate was 97.9% and each yield of sodium hydrogen cis-epoxysuccinate and tartrate were 92.2% and 1.3%.

INDUSTRIAL APPLICABILITY

According to the present invention, it is possible to obtain highly pure acid salts of cis-epoxysuccinic acid in a high yield while suppressing the production of DL-tartrate produced as a by-product. The acid salts of cis-epoxysuccinic acid obtained according to the present invention can easily be converted to cis-epoxysuccinic acid and normal salts of cis-epoxysuccinic acid, which are useful in various applications such as additives of a polymer resin, detergent builders (surfactants) or an intermediate for producing tartaric acid which is one of the representative organic acids, and thus are industrially very important.

What is claimed is:

1. A process for producing a cis-epoxysuccinate comprising epoxidizing a maleate with hydrogen peroxide in the presence of a water-soluble epoxidation catalyst selected from the group consisting of tungstic acid, molybdic acid, heteropolyacids containing tungsten or molybdenum and salts thereof, wherein said epoxidation is carried out in an aqueous solution containing 30–90% by volume of a water-soluble alcohol.

2. The process according to claim 1, wherein said maleate is acid salts of maleic acid.

3. The process according to claim 2, wherein said acid salts of maleic acid are acid salts obtained by reacting maleic anhydride or maleic acid with a base.

4. The process according to claim 2, wherein said acid salts of maleic acid are acid salts obtained by adding maleic anhydride or maleic acid with a base to the epoxidation reaction system, simultaneously.

5. The process according to claim 2, wherein said acid salts of maleic acid are acid salts obtained by adding maleic anhydride or maleic acid simultaneously with normal salts of maleic acid to the epoxidation reaction system, simultaneously.

6. The process according to claim 1, which further comprises adding a calcium compound and an alkali to a solution at least derived from the mother liquor freed of the cis-epoxysuccinate, separating from the resultant solution the tartrate produced as a by-product by precipitating said tartrate in the form of calcium tartrate, and recycling the resulting mother liquor to the reaction system.

* * * * *

UNITED STATES PATENT AND TRADEMARK OFFICE
CERTIFICATE OF CORRECTION

PATENT NO. : 5,608,089
DATED : March 4, 1997
INVENTOR(S) : Keiichi SATO, et al.

It is certified that error appears in the above-indentified patent and that said Letters Patent is hereby corrected as shown below:

On the title page, Item [30], the Foreign Application Priority Data is incorrect. It should read:

-- [30]

Jan. 19, 1993  [JP]  Japan.............5-006839
    May 18, 1993  [JP]  Japan.............5-116212

Signed and Sealed this

Eighth Day of July, 1997

*Attest:*

*Attesting Officer*

BRUCE LEHMAN

*Commissioner of Patents and Trademarks*